United States Patent [19]

Veringa

[11] Patent Number: 5,322,781

[45] Date of Patent: Jun. 21, 1994

[54] **PROCEDURE FOR THE PREPARATION OF D-(−)-LACTIC ACID WITH *LACTOBACILLUS BULGARICUS***

[75] Inventor: Hubertus A. Veringa, Bennekom, Netherlands

[73] Assignee: Cooperatieve Weiproduktenfabriek "Borculo" W.A., Borculo, Netherlands

[21] Appl. No.: 878,541

[22] Filed: May 5, 1992

Related U.S. Application Data

[63] Continuation-in-part of Ser. No. 520,119, May 8, 1990, abandoned, which is a continuation of Ser. No. 972,055, Nov. 4, 1986, abandoned.

[30] Foreign Application Priority Data

Nov. 18, 1985 [NL] Netherlands ............... 8503172

[51] Int. Cl.$^5$ ............... C12P 7/56; C10N 1/38; C12N 1/20
[52] U.S. Cl. ............... 435/139; 435/853; 435/244; 435/252.9
[58] Field of Search ............ 435/139, 853, 244, 252.9

[56] References Cited

U.S. PATENT DOCUMENTS

| | | | |
|---|---|---|---|
| 4,467,034 | 8/1984 | Voelskow | 435/252.9 |
| 4,771,001 | 9/1988 | Bailey et al. | 435/853 |

FOREIGN PATENT DOCUMENTS 0232556  8/1987  European Pat. Off. .

*Primary Examiner*—Irene Marx
*Attorney, Agent, or Firm*—Hopgood, Caliamfde, Kalil, Blaustein & Judlowe

[57] ABSTRACT

The invention relates to a procedure for the preparation of D-(−)-lactic acid in which a strain of *Lactobacillus bulgaricus* capable of converting lactose into D-(−)-lactic acid to an extent of more than 50%, is cultivated in a medium containing lactose. It is known that galactose-positive Lactobacillus strains produce mainly L-lactic acid, and galactose-negative strains produce D-(−)-lactic acid almost exclusively, but leave the galactose part of lactose unchanged, the D-(−)-lactic acid being thereafter recovered. Strains suitable for use in the present procedure are *Lactobacillus bulgaricus* CBS 743.84, CBS 687.85, and CBS 688.85.

11 Claims, No Drawings

PROCEDURE FOR THE PREPARATION OF D-(−)-LACTIC ACID WITH *LACTOBACILLUS BULGARICUS*

This application is a continuation-in-part of U.S. Ser. No. 520,119, filed May 8, 1990, now abandoned, which in turn is a continuation of U.S. Ser. No. 972 055, filed Nov. 4, 1986 (now abandoned).

The invention relates to a process for the preparation of D-(−)-lactic acid by cultivating a strain of *Lactobacillus bulgaricus* in a medium which contains lactose.

BACKGROUND OF THE INVENTION

Such a process is known from the European Patent Application No. 0,072,010. In said known process use is made of the *L. bulgaricus* strain DSM 2129 which appears to be capable of producing D-(−)-lactic acid in high yield in a relatively short time from lactose or glucose. It appears from the description, however, that the strain is not capable of producing acid from galactose, which means that only the glucose part of the lactose is used for the production of the lactic acid and the galactose part remains unchanged.

Hitherto, no strains of Lactobacillus species were known which are galactose-positive and produce D-(−)-lactic acid almost exclusively. It is true that it is reported in Bergey's Manual of Determinative Bacteriology (8th edition) that *L. bulgaricus* is galactose-positive and produces D-(−)-lactic acid almost exclusively, but later investigation revealed that the type strain ATCC 11842 cannot convert any galactose into acid [J. Gen. Microbiol. 74, 289–297 (1973)]. Furthermore, it appears from Appl. Environm. Microbiol. 45, 1932–1934 (1983) that strains of *L. helveticus* and *L. bulgaricus* which are galactose-positive always produce a mixture of D- and L-lactic acid in which the L-isomer predominates, and that strains of *L. lactis* and *L. bulgaricus* which are galactose-negative always produce D-(−)-lactic acid almost exclusively.

STATEMENT OF THE INVENTION

Surprisingly, strains of *L. bulgaricus* have now been found which are in fact capable of converting lactose into D-(−)-lactic acid almost exclusively.

The invention therefore relates to a process for the preparation of D-(−)-lactic acid which comprises cultivating a member selected from the group consisting of *Lactobacillus bulgaricus* strain CBS 743.84, strain CBS 687.85, strain CBS 688.85, a mutant and variant thereof which is capable of converting lactose into D-(−)-lactic acid to an extent of more than 50% in a culture medium containing lactose, under conditions to convert said lactose into D-(−)-lactic acid, and recovering said D-(−)-lactic acid.

The conversion of lactose into D-(−)-lactic acid proceeds more rapidly with *Lactobacillus bulgaricus* strain CBS 743.84 and strain CBS 687.85 than with strain CBS 688.85.

DETAILS OF THE INVENTION

The above-mentioned strains of *Lactobacillus bulgaricus* have been deposited with the Centraal Bureau voor Schimmelcultures in Baarn, the Netherlands. The strains are characterized by the following properties:

|  | CBS 743.84 | *L. bulgaricus* CBS 687.85 | CBS 688.85 |
|---|---|---|---|
| sugar fermentation | homoferm. | homoferm. | homoferm. |
| growth at 15° C. | − | − | − |
| growth at 45° C. | + | + | + |
| acid formed from: | − | − | − |
| amygdalin |  |  |  |
| arabinose | − | − | − |
| cellobiose | − | − | − |
| galactose | + | + | + |
| glucose | + | + | + |
| lactose | + | + | + |
| maltose | − | − | − |
| mannitol | − | − | − |
| melibiose | − | − | − |
| raffinose | − | − | − |
| ribose | − | − | − |
| sucrose | − | − | − |
| salicin | − | − | − |
| sorbitol | − | − | − |
| trehalose | + | − | − |
| xylose | − | − | − |
| configuration of the lactic acid formed | D(−) | D(−) | D(−) |

Said strains are distinguished from the *Lactobacillus bulgaricus* strains isolated from yoghurt by the ability to ferment galactose. Strain CBS 743.84 additionally ferments trehalose. The present strains are distinguished from the known *Lactobacillus bulgaricus* strains which are capable of fermenting galactose by the property of producing D-(−)-lactic acid almost exclusively.

The strains identified by the Accession Nos. CBS 687.85, CBS 688.85, CBS 743.84 have been deposited and accepted under the Budapest Treaty at:

Centraalbureau Voor
Schimmelcultures
P. O. Box 273
3740 AG BAARN
The Netherlands The fermentation of sugar to more than 50% D-(−)-lactic acid by strains CBS 743.84, CBS 687.85 and 688.85 is not limited to the conversion of lactose: glucose and galactose are also converted into D-(−)-lactic acid.

Instead of the above-named strains, according to the invention any variant or mutant thereof may be used provided it is capable of converting lactose into D-(−)-lactic acid to an extent of more than 50%.

The raw material which is used for the preparation of D-(−)-lactic acid has to contain at least lactose but it may also contain other sugars, such as glucose or galactose, to be converted into D-(−)-lactic acid by the microorganism. The most important use is in the preparation of D-(−)-lactic acid from lactose. In particular milk whey which is available in large quantities as a byproduct of cheese and casein preparation is used as a source of lactose. However, the starting product may be a raw material derived from milk, for example a solution or suspension of lactose.

Additional lactose may also be added to other lactose containing products derived from milk such as skimmed milk, an ultrafiltration permeate of milk or milk whey, dissolved whey powder, or even whey which does not usually contain more than approximately 45 g of lactose per litre, in order to achieve a high lactic acid content. The addition of extra lactose can take place both before and during the process, all at once or in batches.

The cultivation of the microorganism is carried out in the manner known for *L. bulgaricus*. In addition to lactose and/or galactose and possibly other fermentable sugars, the medium preferably contains also a source of nitrogen and other substances promoting the growth such as vitamins. Meat extract or, for example, milk protein may serve as the source of nitrogen. The addition of yeast extract as a source of vitamins, trace elements and amino acids is preferred. The growth of the microorganism may also be stimulated by adding formate, carbonate and catalase.

Since the D-(−)-lactic acid produced retards the growth of the microorganism, it is desirable to neutralize the acid during the fermentation in a manner such that the pH is held at a value of at least 5.0, preferably at a value of 6.0–7.0. This can be done in a known manner by gradually adding a base such as ammonia, a hydroxide such as sodium, potassium or calcium hydroxide (lime water) or alkali-metal or alkaline-earth metal carbonates, in particular calcium carbonate. A calculated quantity of calcium carbonate can be added all at once at the beginning of the fermentation. It gradually dissolves as more D-(−)-lactic acid is formed. As a result the pH remains in the required region.

It may also be beneficial to add a surface active agent such as an epoxyethane or epoxypropane addition product of a long chain alcohol or acid. Examples of said agents are the products which are marketed under the trademarks of Tween ® and Span ®.

The isolation of the lactic acid from the fermentation medium is also carried out in a manner known per se. Thus, if a calcium compound, for example calcium carbonate has been used to control the pH during the fermentation, the calcium lactate produced can be converted into D-(−)-lactic acid via reaction with sulphuric acid, the calcium sulphate formed being filtered off and the filtrate concentrated by evaporation.

The invention is explained in more detail on the basis of the following examples.

EXAMPLE I

A medium I was prepared on the basis of whey ultrafiltration permeate. To said permeate (containing 5% (m/v) dry substance) the following were added:
10% (v/v) skimmed milk;
1% (m/v) yeast extract;
0.1% (v/v) Tween-80;
phosphate (1.1 g of $Na_2HPO_4.2H_2O$ + 1.2 g of $KH_2PO_4$ per litre);
0.002% (m/v) sodium formate;
0.01% (m/v) sodium carbonate;
catalase (2 Keil units per litre).

The lactose content of said medium was approximately 4.3% (m/v).

After pasteurizing the medium and cooling it to cultivation temperature (37° C.) in a cultivation vessel, the medium was inoculated with 1% (v/v) culture of *Lactobacillus bulgaricus*, strain CBS 743.84; the pH of the mixture was adjusted to a value of 6.0 by means of an ammonia solution. The pH was kept at the value of 6.0 during the cultivation by automatic metered addition of the ammonia solution, the mixture being continuously stirred. During the cultivation the conversion of the lactose was followed by measuring the consumption of ammonia. From the consumption of ammonia it was possible to calculate that if each molecule of lactose were to produce four molecules of lactic acid, 89.8% lactose had been converted after 22 hours. Enzymatic determination of the lactic acid formed indicated that after 22 hours over 85% of the quantity of lactose present at the start had in fact been converted into lactic acid, the acid being recovered by known methods.

Over 99% of the lactic acid formed appeared to consist of the D-(−)-isomer.

EXAMPLE II

A medium II was prepared consisting of centrifuged mixed whey to which the following were added:
10% (v/v/) skimmed milk;
1% (m/v) yeast extract;
0.1% (v/v) Tween-80;
phosphate (1.1 g of $Na_2HPO_4.2H_2O$ + 1.2 g of $KH_2PO_4$ per litre);
0.008% (m/v) sodium formate;
0.01% (m/v) sodium carbonate;
catalase (4.Keil units per litre).

The lactose content of the medium was raised to 9.26% (m/v) by adding lactose.

*Lactobacillus bulgaricus*, strain CBS 743.84, was cultivated in said medium in the manner as indicated in Example I.

At set times the lactose conversion percentage was calculated from the quantity of ammonia consumed at that instant; in addition, the quantities of lactose, galactose and lactic acid were measured at some time instants. Some of the results are summarized in Table A.

The quantities of lactic acid quoted therein have been corrected for the quantities of lactic acid already present at the beginning of the test. Column A records the lactose conversion percentage calculated from the consumption of ammonia, column B records the calculated quantity of lactic acid which would have been produced from the quantity of lactose converted after correction for the residual quantity of galactose; column C gives the quantity of lactic acid actually formed as a percentage of the corresponding calculated quantity in column B.

TABLE A

| Cultivation time (h) at 37° C. | Content (g/l) | | Lactic acid produced (g/l) | | | A (%) | B (g/l) | C (%) |
| --- | --- | --- | --- | --- | --- | --- | --- | --- |
| | lactose | galactose | D(−) | L(+) | Total | | | |
| 0 | 92.6 | 0.6 | 0 | 0 | 0 | 0 | 0 | |
| 16¼ | 12.4 | 27.6 | 53.5 | 2.2 | 55.7 | 60.5 | 57.4 | 97 |
| 19½ | | | | | | 71.5 | | |
| 21½ | | | | | | 77.3 | | |
| 24¼ | 4.1 | 11.6 | 77.0 | 3.8 | 80.8 | 85.0 | 82.2 | 98 |
| 40¼ | 0.1 | 2.6 | 80.3 | 5.6 | 85.9 | 100.6 | 95.4 | 90 |
| 48½ | | | | | | 100.6 | | |

EXAMPLE III

A semi-synthetic medium (TGV) was prepared which consisted of:
1% (m/v) trypton;
0.3% (m/v) meat extract 0.5% (m/v) yeast extract;
4% (v/v) tomato juice;
0.1% (v/v) Tween-80;
0.2% (m/v) of $K_2HPO_4$.

In addition, in one case 4.1% (m/v) lactose was added (TGV lactose), and in another case 4.5% (m/v) glucose (TGV glucose).

*Lactobacillus bulgaricus,* strain CBS 743.84, was cultivated in said media in the manner indicated in Example I, but at 44° C. instead of at 37° C.

At set times the lactose conversion percentage was calculated from the quantity of ammonia consumed at that instant. After 26 hours 94% lactose was found to have been converted, and after 42 hours around 98%; glucose had already been completely converted after 26 hours. Some other results of said experiment are quoted in Table B. Column A records the lactose conversion percentage calculated from the consumption of ammonia, and column B the calculated quantity of lactic acid which would have been produced from the quantity of lactose converted, after correction for the residual quantity of galactose. Column C gives the quantity of lactic acid actually formed as a percentage of the calculated quantity in column B.

TABLE B

| Medium | Cultivation time (h) at 44° C. | Lactose g/l | Galactose g/l | Glucose g/l | Lactic acid produced (g/l) D(−) | L(+) | total | A % | B g/l | C % |
|---|---|---|---|---|---|---|---|---|---|---|
| TGV lactose | 0 | 40.7 | 0.3 | 0.5 | 0 | 0 | 0 | 0 | | |
| | 27 | 0.1 | 2.0 | 0.0 | 34.7 | 0.1 | 34.8 | ·97 | 41.5 | 84 |
| TGV glucose | 0 | 0.6 | 0.3 | 45.3 | 0 | 0 | 0 | 0 | | |
| | 27 | 0.0 | 0.4 | 0.0 | 35.6 | 1.2 | 36.8 | 101 | 45.8 | 80 |

EXAMPLE IV

Various pasteurized media (a–k) were inoculated with 1% (v/v) of a culture of *Lactobacillus bulgaricus*, strain CBS 743.84. At set times during the cultivation at 37° C. the degree of acidity and the pH were determined (in the tests in this example the pH was therefore not kept constant). The increase in the degree of acidity (expressed in °N: the number of ml of 0.1N hydroxide necessary to neutralize 100 ml of mixture) was taken as a measure of the lactic acid formation.

The compositions of the media used are given in Table C and the results are reproduced in Table D.

TABLE C

| Constituents | a | b | c | d | e | f | g | h | i | j | k |
|---|---|---|---|---|---|---|---|---|---|---|---|
| Lactose, Analar, 10% (m/v) | + | − | − | − | − | − | − | − | − | − | − |
| Lactose, "edible quality", 10% (m/v) | − | + | + | + | + | + | + | + | + | + | + |
| Sodium formate, 0.002% (m/v) | − | − | + | + | + | + | + | + | + | + | + |
| Tween-80, 0.1% (v/v) | − | − | + | + | + | + | + | + | + | + | + |
| Sodium carbonate, 0.1% (v/v) | − | − | + | + | + | + | + | + | + | + | + |
| 4.4 g $Na_2HPO_4$·$2H_2O$ + 4.8 g $KH_2PO_4$ per liter | − | − | − | + | + | + | + | + | + | + | + |
| Skimmed milk, 10% (v/v) | − | − | − | − | + | − | + | − | + | − | + |
| Catalase (2 Keil units per liter) | − | − | − | − | − | + | + | − | − | + | + |
| Yeast extract, 1% (m/v) | − | − | − | − | − | − | − | + | + | + | + |

TABLE D

| Medium | pH after cultivation time of | | | |
|---|---|---|---|---|
| | 0 h | 19 h | 23.5 h | 43 h |
| a | 5.96 | 4.40 | 4.38 | 4.30 |
| b | 5.77 | 4.43 | 4.37 | 4.37 |
| c | 7.91 | 7.53 | 7.51 | 7.49 |
| d | 6.77 | 6.76 | 6.73 | 6.69 |
| e | 6.75 | 6.72 | 6.70 | 6.63 |
| f | 6.75 | 6.65 | 6.62 | 6.58 |
| g | 6.73 | 5.85 | 4.92 | 4.11 |
| h | 6.73 | 4.18 | 4.12 | 4.01 |
| i | 6.71 | 4.15 | 4.03 | 3.93 |
| j | 6.72 | 4.14 | 4.06 | 4.01 |
| k | 6.71 | 4.04 | 3.91 | 3.86 |

| Medium | Degree of acidity after cultivation time of | | | |
|---|---|---|---|---|
| | 0 h | 19 h | 23.5 h | 43 h |
| a | 1.6 | 2.3 | 2.6 | 2.4 |
| b | 0.9 | 1.6 | 1.9 | 1.8 |
| c | 0.4 | 0.4 | 0.3 | 0.2 |
| d | 28.9 | 29.0 | 28.7 | 28.2 |
| e | 31.2 | 32.0 | 32.0 | 31.8 |
| f | 28.9 | 30.5 | 31.2 | 31.1 |
| g | 30.8 | 50.3 | 61.3 | 76.0 |
| h | 35.8 | 88.3 | 88.6 | 90.2 |
| i | 37.2 | 99.0 | 105.1 | 110.2 |
| j | 34.7 | 89.2 | 89.1 | 90.1 |
| k | 37.6 | 107.4 | 113.5 | 115.3 |

EXAMPLE V

A medium was prepared which had the same composition as medium II in Example II, but with the difference that the lactose content of the medium was raised not to 9.26%, but to 7.5% (m/v) by adding lactose.

*Lactobacillus bulgaricus* CBS 743.84 was cultivated in said medium in the manner described in Example I. The conversion was determined by measuring the consumption of ammonia. After 23 h, when 97% of the lactose was found to have been converted, a further 1% (m/v) lactose was added, 100% of which quantity was found to have been converted after 41 h.

EXAMPLE VI

A medium II was prepared consisting of centrifuged mixed whey to which the following were added:
10% (v/v) skimmed milk;
1% (m/v) yeast extract
0.1% (v/v) Tween-80;
phosphate (1.1 g of $Na_2HPO_4.2H_2O$ + 1.2 g of $KH_2PO_4$ per litre);
0.008% (m/v) sodium formate;
0.01% (m/v) sodium carbonate;
catalase (4 Keil units per litre).

The lactose content of the medium was raised to 7.8% (m/v) by adding lactose.

After pasteurizing the medium and cooling it to cultivation temperature (37° C.) in a cultivation vessel, the medium was inoculated with 1% (v/v) culture of *Lactobacillus bulgaricus*, strain CBS 687.85; the pH of the mixture was adjusted to a value of 6.0 by means of an ammonia solution. The pH was kept at the value of 6.0 during the cultivation by automatic metered addition of the ammonia solution, the mixture being continuously stirred. During the cultivation the conversion of the lactose was followed by measuring the consumption of ammonia. From the consumption of ammonia the lactose conversion was calculated as follows:

After 21.25 hours: 88.0%
After 49.5 hours: 94.7%
After 64.5 hours: 100%

More than 90% of the lactic acid formed consisted of the D-(−)-isomer.

Example VII

A medium II was prepared consisting of centrifuged mixed whey to which the following were added:
10% (v/v) skimmed milk;
1% (m/v) yeast extract
0.1% (v/v) Tween-80;
phosphate (1.1 g of $Na_2HPO_4.2H_2O$ + 1.2 g of $KH_2PO$ per litre);
0.008% (m/v) sodium formate;
0.01% (m/v) sodium carbonate;
catalase (4 Keil units per litre).

The lactose content of the medium was raised to 7.8% (m/v) by adding lactose.

After pasteurizing the medium and cooling it to cultivation temperature (37° C.) in a cultivation vessel, the medium was inoculated with 1% (v/v) culture of *Lactobacillus bulgaricus*, strain CBS 688.85; the pH of the mixture was adjusted to a value of 6.0 by means of an ammonia solution. The pH was kept at the value of 6.0 during the cultivation by automatic metered addition of the ammonia solution, the mixture being continuously stirred. During the cultivation the conversion of the lactose was followed by measuring the consumption of ammonia. From the consumption of ammonia the lactose conversion was calculated as follows:

After 21.25 hours: 53.5%
After 49.5 hours: 69.7%
After 64.5 hours: 72.9%
After 73.25 hours: 74.4%

More than 90% of the lactic acid formed consisted of the D-(−)-isomer.

What is claimed is:

1. A process for preparing D-(−)-lactic acid which comprises cultivating a member selected from the group consisting of *Lactobacillus bulgaricus* strain CBS 743.84, strain CBS 687.85, strain CBS 688.85 and a mutant thereof which is capable of converting lactose into D-(−)- lactic acid to an extent greater than 50% in a culture medium containing lactose, under conditions sufficient to convert said lactose into D-(−)-lactic acid, and recovering said D-(−)-lactic acid.

2. The process according to claim 1, in which said culture medium comprises a lactose containing culture medium derived from milk.

3. The process according to claim 2, in which said culture medium comprises milk whey.

4. The process according to claim 3, in which said culture medium comprises an ultrafiltration permeate of milk whey.

5. The process according to claim 2, in which in addition to the lactose derived from milk, said culture medium contains additional lactose.

6. The process according to claim 1, in which lactose is added to said culture medium during the cultivation.

7. The process according to claim 1, in which the culture medium contains growth-stimulating substances.

8. The process to claim 1 in which the cultivation is carried out at a pH of at least about 5.0.

9. The process according to claim 8, in which the cultivation is carried out a temperature of about 30°–45° C.

10. The process according to claim 8, wherein cultivation is carried out at a pH of about 6 to 7.

11. The process of claim 9, wherein the cultivation is carried out at a temperature of about 35°–40° C.

* * * * *